United States Patent
Su et al.

(10) Patent No.: US 12,239,479 B2
(45) Date of Patent: Mar. 4, 2025

(54) SYSTEMS AND METHODS FOR NON-INVASIVE PRESSURE MEASUREMENTS

(71) Applicant: KONINKLIJKE PHILIPS N.V., Eindhoven (NL)

(72) Inventors: Jimmy Li-Shin Su, Arlington, MA (US); David Prater, Andover, MA (US); Patrick Gabriels Rafter, Windham, NH (US); Alexandra Goncalves, Cambridge, MA (US); Lydia Rivera, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 340 days.

(21) Appl. No.: 17/918,152

(22) PCT Filed: Apr. 13, 2021

(86) PCT No.: PCT/EP2021/059471
§ 371 (c)(1),
(2) Date: Oct. 11, 2022

(87) PCT Pub. No.: WO2021/209400
PCT Pub. Date: Oct. 21, 2021

(65) Prior Publication Data
US 2023/0134503 A1 May 4, 2023

Related U.S. Application Data

(60) Provisional application No. 63/010,748, filed on Apr. 16, 2020.

(51) Int. Cl.
A61B 8/04 (2006.01)
A61B 8/00 (2006.01)
A61B 8/08 (2006.01)

(52) U.S. Cl.
CPC .............. *A61B 8/04* (2013.01); *A61B 8/0883* (2013.01); *A61B 8/483* (2013.01); *A61B 8/485* (2013.01); *A61B 8/5223* (2013.01)

(58) Field of Classification Search
CPC ......... A61B 8/04; A61B 8/0833; A61B 8/483; A61B 8/485; A61B 8/5223
See application file for complete search history.

(56) References Cited

U.S. PATENT DOCUMENTS 6,443,896 B1 9/2002 Detmer
6,530,885 B1 3/2003 Entrekin et al.
(Continued)

FOREIGN PATENT DOCUMENTS

WO 2017006236 A1 1/2017
WO 2017205836 A1 11/2017

OTHER PUBLICATIONS

International Search Report and Written Opinion for PCT/EP2021/059471; Mailing date: Jul. 5, 2021, 9 pages.
(Continued)

*Primary Examiner* — Gerald Johnson

(57) ABSTRACT

An ultrasound imaging system may acquire ultrasound data from a heart. The ultrasound data may be analyzed to on-invasively provide a value for cardiac pressure, such as left ventricular end diastolic pressure (LVEDP). In some examples, the ultrasound data may be acquired from B-mode images, Doppler images, and/or strain measurements. In some examples, the ultrasound data may be acquired across an entire cardiac cycle of the heart. In some examples, the ultrasound data may include strain measurements and/or volume measurements of the left atrium. In some examples, the ultrasound data may be analyzed by a correlation algorithm, such as a partial least squares model and/or a neural network.

18 Claims, 5 Drawing Sheets

(56) References Cited

U.S. PATENT DOCUMENTS

| | | |
|---|---|---|
| 2013/0245441 A1 | 9/2013 | Datta |
| 2015/0005629 A1 | 1/2015 | Monahan et al. |
| 2015/0028684 A1 | 1/2015 | Harrison et al. |
| 2016/0249880 A1* | 9/2016 | Konofagou ............ G16H 50/30 600/438 |
| 2018/0192987 A1* | 7/2018 | Salgo .................. A61B 8/5207 |

OTHER PUBLICATIONS

Kawasaki, M. et al., "A novel ultrasound predictor of pulmonary capillary wedge pressure assessed by the combination of left atrial volume and function: A speckle tracking echocardiography study", J Cardiol., 2015, vol. 66, pp. 253-262.

Nagueh, S.F. et al., "Doppler Tissue Imaging: A Noninvasive Technique for Evaluation of Left Ventricular Relaxation and Estimation of Filling Pressures", Journal of the American College of Cardiology, 1997, vol. 30, pp. 1527-1533.

Cameli, M., "Left atrial longitudinal strain by speckle tracking echocardiography correlates well with left ventricular filling pressures in patients with heart failure", Cardiovascular Ultrasound, 2010, vol. 8, 9 pages.

Singh, A. et al., "Peak left atrial strain as a single measure for the non-invasive assessment of left ventricular filling pressures", Int J Cardiovasc Imaging., 2019, vol. 35, pp. 23-32.

Krizhevsky, A. et al., "ImageNet Classification with Deep Convolutional Neural Networks", NIPS 2012, 9 pages.

Iwase, M. et al., "Noninvasive detection of exercise-induced markedly elevated left ventricular filling pressure by pulsed Doppler echocardiography in patients with coronary artery disease," American Heart Journal, 1989, vol. 118, Issue 5, pp. 947-954.

* cited by examiner

SYSTEMS AND METHODS FOR NON-INVASIVE PRESSURE MEASUREMENTS

CROSS-REFERENCE TO PRIOR APPLICATIONS

This application is the U.S. National Phase application under 35 U.S.C. § 371 of International Application No PCT/EP2021/059471, filed on Apr. 13, 2021, which claims the benefit of U.S. Provisional Patent Application No. 63/010,748, filed on Apr. 16, 2020. These applications are hereby incorporated by reference herein.

TECHNICAL FIELD

The present disclosure pertains to imaging systems and methods for non-invasively measuring pressure. More specifically, the present disclosure pertains to analyzing ultrasound data to non-invasively measure left ventricular pressure.

BACKGROUND

Left ventricular end diastolic pressure (LVEDP) is an important clinical measure to determine ventricular function, and this measure can help physicians determine patients who are at risk for late stage cardiac failure. LVEDP is traditionally obtained through left heart catheterization, which is an invasive procedure and requires additional time and resources that could be spent treating the patient. It would be desirable to obtain LVEDP through non-invasive methods. Several methods have been previously proposed based on simple regression techniques that involve manual selection of a small number of input parameters and then somewhat optimized amongst these parameters. However, these methods are not ideal for such a multi-dimensional problem that is affected by many different aspects over the cardiac cycle, especially when two or more of the input parameters may not be independent.

SUMMARY

As disclosed herein, LVEDP or other pressures, such as filling pressure and pulmonary capillary wedge pressure (PCWP), may be non-invasively measure through ultrasound data acquired from a heart, such as from left atrium (LA) and/or left ventricle (LV). Examples of ultrasound data may include strain and/or volume information of the LA and/or LV. A correlation algorithm between the ultrasound data and invasive catheter pressure may be used to determine a value for the pressure. In some examples, the ultrasound data may be preprocessed prior to training the correlation algorithm (e.g., clean-up of the input LA strain signal versus time for one cardiac cycle). Once the data has been preprocessed, the resulting data may be input into the correlation algorithm, which may include a model, such as a deep learning model, a machine learning model, artificial intelligence, and/or other model. In some examples, the model may include a set of regression coefficients that have been developed through training the model. In some examples, the model may be a Partial Least Squares (PLS) model and/or a long short-term memory (LSTM) network. In one example, the ultrasound data may be correlated to the actual pressure output as measured by the pressure catheter. In another example, the ultrasound data may be correlated to a classifier, for example, high/medium/low thresholds of pressure that may be clinically relevant.

An ultrasound imaging system according to an example of the present disclosure may include a processor configured to receive ultrasound data of a heart, wherein the ultrasound data was acquired across at least a portion of a cardiac cycle and analyze the ultrasound data by applying a correlation algorithm to determine a value of cardiac pressure.

A method according to an example of the present disclosure may include receiving ultrasound data of a heart, wherein the ultrasound data was acquired across a cardiac cycle and analyzing the ultrasound data by applying a correlation algorithm to determine a value of cardiac pressure.

In accordance with an example of the present disclosure, a non-transitory computer-readable medium may contain instructions, that when executed, may cause an imaging system to receive ultrasound data of a heart, wherein the ultrasound data was acquired across at least a portion of a cardiac cycle and analyze the ultrasound data by applying a correlation algorithm to determine a value of cardiac pressure

DETAILED DESCRIPTION

Figure 1:
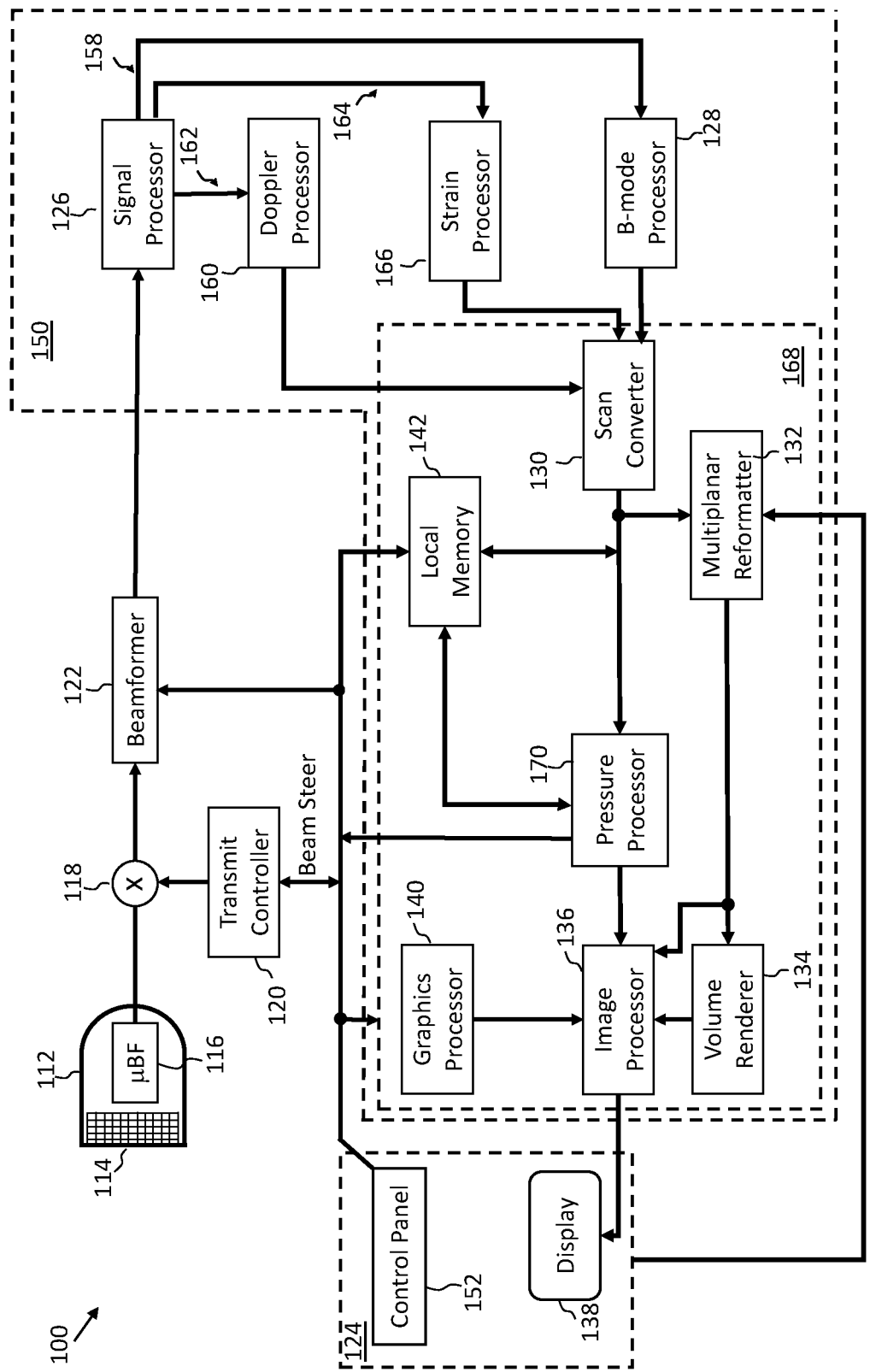
FIG. 1 is a block diagram of an ultrasound system in accordance with principles of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

As described by Kawasaki et al., the left pulmonary capillary wedge pressure (PCWP) value is correlated to several aspects of the left atrium (LA) volume cycle. Kawasaki ran multiple iterations of a regression test to see which LA volume parameters would correlate the best with the PCWP catheter pressure value. In the end, Kawasaki chose one combination of two parameters to create what is known in the paper as the "KT index". See M. Kawasaki et al. "A novel ultrasound predictor of pulmonary capillary wedge pressure assessed by the combination of left atrial volume and function: A speckle tracking echocardiography study," J. Cardiol., vol 66. No. 3, pp. 253-262, 2015. This method, while manually optimized, ignores all the other parameters that also showed correlation to catheter pressure. To include these would have created a multi-dimensional regression equation. However, multi-dimensional linear regression cannot be used if the independent, input parameters are linearly correlated with one another, which the LA volume parameters are found to be, in this case. Furthermore, the input parameters used by Kawasaki are fraught with noise, and are not cleaned up prior to being used in his regression equation.

Additionally, it has been shown that left ventricular end diastolic pressure (LVEDP) is directly related to left atrial strain information. Previous publications have shown correlation by manual linear regression methods alone (See e.g., M. Cameli et al., "Left atrial longitudinal strain by speckle tracking echocardiography correlates well with left ventricular filling pressures in patients with heart failure," Cardiovascular Ultrasound, vol 8. No 14. 2010 and A. Singh et al., "Peak left atrial strain as a single measure for the non-invasive assessment of left ventricular filling pressures," Int J Cardiovasc Imaging, vol 35. No 1. 2019. These additional methods that develop a relationship between ventricular pressure and strain operate similarly to the LA volume methods described by Kawasaki.

A non-invasive solution that can take advantage of the information provided by multiple parameters, regardless of whether or not the parameters are independent, across multiple phases of the cardiac cycle (e.g., from early diastole to late systole, from early diastole of a first heartbeat to early diastole of a second heartbeat, etc.) is desired.

According to principles of the present disclosure, ultrasound data acquired from a heart, such as from the LA or left ventricle (LV), may be provided to a correlation algorithm, which may include a model (e.g., machine learning, deep learning, artificial intelligence, algorithm). The model may determine a cardiac pressure (e.g., LVEDP, LV filling pressure, PCWP, Pre-A Pressure) based on the provided ultrasound data. Examples of ultrasound-derived data from the heart that may be provided to the model include, but are not limited to, tissue strain measurements (e.g., longitudinal strain, circumferential strain) and volume. In some examples, the model may include a partial least squares (PLS) model. In some examples, the model may be trained to generate a transfer function which may be used to determine the pressure based on the provided ultrasound data. In some examples, the transfer function may include one or more regression coefficients. In some examples, the model may include a neural network, such as a long short-term memory (LSTM) network. In some examples, the model may output a numeric value for the pressure. In some examples, the model may output a classifier that provides a qualitative indication of the pressure (e.g., normal, mild, moderate, severe).

In some examples, the ultrasound data may be preprocessed prior to being provided to the model. In some examples, the ultrasound data may be interpolated to a pre-set number of frames across a cardiac cycle. In some examples, the pre-set number of frames may be evenly spaced across the cardiac cycle. In some examples, the cardiac cycle may be sub-divided into different phases of the LA (i.e. reservoir, conduit and contraction phases), LV, and/or other portion of the heart. In some examples, these phases may each be interpolated to a pre-set number of frames individually, and then combined together. In some examples, the pre-set number of frames may be selected from desired phases of the cardiac cycle (e.g., early atrial systole, late atrial diastole). The length and/or phases of the cardiac cycle may be determined based on ultrasound imaging (e.g., B-mode or Doppler) and/or based on electrocardiography (ECG) signals (e.g., detecting the QRS wave complex). In some examples, the ultrasound data may be smoothed by a filter, such as a Savitsky-Golay filter. In some examples, the filtering may be performed after the interpolation.

The systems and methods disclosed herein may provide a non-invasive technique for determining pressure that utilizes multiple parameters over an entire phase of the cardiac cycle, multiple phases of the cardiac cycle, an entire cardiac cycle, and/or multiple cardiac cycles. In some applications, this may provide more accurate and/or consistent measurements of pressure than existing non-invasive methods.

FIG. 1 shows a block diagram of an ultrasound imaging system 100 constructed in accordance with the principles of the present disclosure. An ultrasound imaging system 100 according to the present disclosure may include a transducer array 114, which may be included in an ultrasound probe 112, for example an external probe or an internal probe such as an Intra Cardiac Echography (ICE) probe or a Trans Esophagus Echography (TEE) probe. In other embodiments, the transducer array 114 may be in the form of a flexible array configured to be conformably applied to a surface of subject to be imaged (e.g., patient). The transducer array 114 is configured to transmit ultrasound signals (e.g., beams, waves) and receive echoes responsive to the ultrasound signals. A variety of transducer arrays may be used, e.g., linear arrays, curved arrays, or phased arrays. The transducer array 114, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some embodiments, the transducer array 114 may be coupled to a microbeamformer 116, which may be located in the ultrasound probe 112, and which may control the transmission and reception of signals by the transducer elements in the array 114. In some embodiments, the microbeamformer 116 may control the transmission and reception of signals by active elements in the array 114 (e.g., an active subset of elements of the array that define the active aperture at any given time).

In some embodiments, the microbeamformer 116 may be coupled, e.g., by a probe cable or wirelessly, to a transmit/receive (T/R) switch 118, which switches between transmission and reception and protects the main beamformer 122 from high energy transmit signals. In some embodiments, for example in portable ultrasound systems, the T/R switch 118 and other elements in the system can be included in the ultrasound probe 112 rather than in the ultrasound system base, which may house the image processing electronics. An ultrasound system base typically includes software and hardware components including circuitry for signal processing and image data generation as well as executable instructions for providing a user interface (e.g., processing circuitry 150 and user interface 124).

The transmission of ultrasonic signals from the transducer array 114 under control of the microbeamformer 116 is directed by the transmit controller 120, which may be coupled to the T/R switch 218 and a main beamformer 122. The transmit controller 120 may control the direction in which beams are steered. Beams may be steered straight ahead from (orthogonal to) the transducer array 114, or at different angles for a wider field of view. The transmit controller 120 may also be coupled to a user interface 124 and receive input from the user's operation of a user control. The user interface 124 may include one or more input devices such as a control panel 152, which may include one or more mechanical controls (e.g., buttons, encoders, etc.), touch sensitive controls (e.g., a trackpad, a touchscreen, or the like), and/or other known input devices.

In some embodiments, the partially beamformed signals produced by the microbeamformer 116 may be coupled to a main beamformer 122 where partially beamformed signals from individual patches of transducer elements may be combined into a fully beamformed signal. In some embodiments, microbeamformer 116 is omitted, and the transducer array 114 is under the control of the main beamformer 122 which performs all beamforming of signals. In embodiments with and without the microbeamformer 116, the beamformed signals of the main beamformer 122 are coupled to processing circuitry 150, which may include one or more processors (e.g., a signal processor 126, a B-mode processor 128, a Doppler processor 160, and one or more image generation and processing components 168) configured to produce an ultrasound image from the beamformed signals (e.g., beamformed RF data).

The signal processor 126 may be configured to process the received beamformed RF data in various ways, such as bandpass filtering, decimation, I and Q component separation, and harmonic signal separation. The signal processor 126 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 158 which couples the signals from the signal processor 126 to a B-mode processor 128 for producing B-mode image data.

The B-mode processor can employ amplitude detection for the imaging of structures in the body. The signals produced by the B-mode processor 128 may be coupled to a scan converter 130 and/or a multiplanar reformatter 132. The scan converter 130 may be configured to arrange the echo signals from the spatial relationship in which they were received to a desired image format. For instance, the scan converter 130 may arrange the echo signal into a two dimensional (2D) sector-shaped format, or a pyramidal or otherwise shaped three dimensional (3D) format. The multiplanar reformatter 132 can convert echoes which are received from points in a common plane in a volumetric region of the body into an ultrasonic image (e.g., a B-mode image) of that plane, for example as described in U.S. Pat. No. 6,443,896 (Detmer). The scan converter 130 and multiplanar reformatter 132 may be implemented as one or more processors in some embodiments.

A volume renderer 134 may generate an image (also referred to as a projection, render, or rendering) of the 3D dataset as viewed from a given reference point, e.g., as described in U.S. Pat. No. 6,530,885 (Entrekin et al.). The volume renderer 134 may be implemented as one or more processors in some embodiments. The volume renderer 134 may generate a render, such as a positive render or a negative render, by any known or future known technique such as surface rendering and maximum intensity rendering.

In some embodiments, the system may include a Doppler signal path 162 which couples the output from the signal processor 126 to a Doppler processor 160. The Doppler processor 160 may be configured to estimate the Doppler shift and generate Doppler image data. The Doppler image data may include color data which is then overlaid with B-mode (i.e. grayscale) image data for display. The Doppler processor 160 may be configured to filter out unwanted signals (i.e., noise or clutter associated with non-moving tissue), for example using a wall filter. The Doppler processor 160 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some embodiments, the velocity and/or power estimates may undergo further threshold detection to further reduce noise, as well as segmentation and post-processing such as filling and smoothing. The velocity and/or power estimates may then be mapped to a desired range of display colors in accordance with a color map. The color data, also referred to as Doppler image data, may then be coupled to the scan converter 230, where the Doppler image data may be converted to the desired image format and overlaid on the B-mode image of the tissue structure to form a color Doppler or a power Doppler image. In some examples, the scan converter 130 may align the Doppler image and B-mode image In some embodiments, the system 100 may include a strain imaging signal path 164 which couples the signals from the signal processor 126 to a strain processor 166 for producing strain measurements. The strain measurements may include elastic shear modulus, Young modulus, and/or other strain measurements. In some examples, the strain measurements may be mapped to pixel color and/or intensity values to generate maps (e.g., strain maps) that may be overlaid onto B-mode and/or Doppler images. In some examples, the scan converter 130 may align the strain measurements with the B-mode and/or Doppler images.

In some examples, the strain measurements may be obtained by shear wave elastography (SWE). In SWE, the probe 112 may transmit an ultrasound signal "push pulse" that induces a shear wave in an object (e.g., tissue). Alternatively, the shear wave in the object may be generated without acoustic radiation force but via mechanical force applied externally to the object, such as by a mechanical vibrator (not shown) that compresses the object. The probe 112 may transmit additional ultrasound signals "tracking pulses" in the object at and/or adjacent to a location where the push pulse was transmitted. Echoes responsive to the tracking pulses may be received by the probe 112. Signals based on the echoes may be analyzed by the strain processor 166 to determine various properties of the shear wave as it propagated through the locations of the tracking pulses in the object. The strain processor 166 may calculate a peak displacement, phase, velocity, and/or other features of the shear wave at one or more locations of the tracking pulses. These features of the shear wave may then be used by the strain processor 166 to calculate material properties of the object at the location of the push pulse and/or location(s) of the tracking pulses. For example, the velocity of the shear wave may be used to determine the shear modulus and/or the Young modulus. In some examples, B-mode signals and/or RF-signals may be provided to the strain processor 166 for analysis to generate strain measurements. For example, correlation between RF echo signals of different windows before and after compression may be used to determine tissue displacement. The tissue displacement may be used to calculate normal strain in some examples. In another example, speckle tracking in B-mode signals may be used to determine particle motion and/or tissue displacement. In some examples, the velocity of the particle motion may be used to calculate the bulk modulus. Other techniques of calculating strain measurements may also be used (e.g., acoustic radiation force impulse strain imaging, transient elastography).

According to embodiments of the present disclosure, output from the scan converter 130, such as B-mode images, Doppler images, strain measurements, and/or strain maps, may be provided to a pressure processor 170. The pressure processor 170 may analyze the ultrasound images, strain measurements, and/or strain maps for ultrasound data to determine a value for a cardiac pressure (e.g., mmHg). Cardiac pressure may include, but is not limited to, LVEDP, LV filling pressure, and/or PCWP.

In some examples, the ultrasound data may include volume. In some examples, the pressure processor 170 may receive a sequence of 2D B-mode images acquired across a cardiac cycle, a portion of a cardiac cycle, and/or multiple cardiac cycles. The sequence may have been acquired at a same imaging plane. The pressure processor 170 may analyze the 2D B-mode images to find a border of the LA and/or other chambers of the heart. The border may be found using any suitable technique. For example, the border may be found using 2D Cardiac Performance Analysis provided by TOMTEC. Once the border has been determined, a volume of the chamber may be estimated, for example, using Simpson's method of disks technique. In some examples, the pressure processor 170 may receive a sequence of 3D B-mode volume images across a cardiac cycle. The pressure processor 170 may analyze the 3D B-mode volumes to find the heart chamber volume directly. The volume may be found using any suitable technique, for example, using the HeartModel$^{A.I.}$ developed by Koninklijke Philips. Thus, the volume for the heart chamber(s) for multiple time-points across the cardiac cycle may be obtained.

Figure 4:
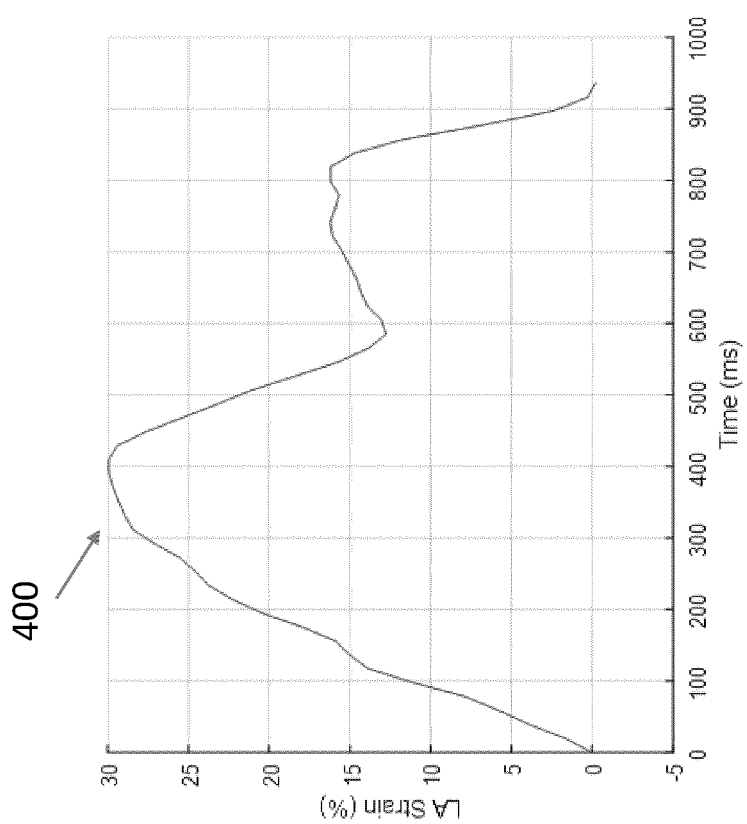
FIG. 4 is an example of a strain curve in accordance with the principles of the present disclosure.

In some examples, the pressure processor 170 may receive a sequence of strain maps and/or strain measurements acquired at different time points across a cardiac cycle, a portion of a cardiac cycle, and/or multiple cardiac cycles. The strain maps and/or strain measurements may be analyzed by the pressure processor 170 to generate a strain curve. The strain curve plots strain measurements over time. The strain curve may be for longitudinal or circumferential strain in some examples. An example longitudinal strain curve 400 for the LA is shown in FIG. 4. The example strain curve 400 reflects the percentage strain of the LA tissue over time in milliseconds. The strain curve may be generated by any suitable technique, for example, using AutoStrain available from TOMTEC.

The ultrasound data, such as the volume and/or strain, may be analyzed by the pressure processor 170 to determine a value for the pressure. In some examples, the ultrasound data may be preprocessed prior to being analyzed. In some applications, preprocessing the data may increase consistency in the data across data sets and/or reduce noise that may affect the determination of the pressure. In some examples, the ultrasound data may be interpolated to a pre-set number of frames across a desired acquisition length (e.g., an entire cardiac cycle, one or more phases of the cardiac cycle, multiple cardiac cycles). In some examples, interpolating may be used to increase the number of frames analyzed by the pressure processor 170 compared to the original number of frames acquired. In some examples, interpolating may ensure that a same number of data points are analyzed by the pressure processor 170 each time. In some examples, this may help improve consistency as to how the analyzed data points are distributed across the acquisition period. The pre-set number of frames may be pre-programmed in the ultrasound imaging system 100 and/or may be selected by a user via the user interface 124. In some examples, when ultrasound images are acquired over multiple cardiac cycles, the frames over the cardiac cycles may be averaged prior to interpolation. In other examples, interpolation may be performed for each cardiac cycle and the interpolated frames for the cardiac cycles may be averaged.

In some examples, the ultrasound data may be filtered. In some examples, the ultrasound data may be smoothed by a digital filter. An example of a suitable filter is a Savitsky-Golay filter. In some examples, the Savitsky-Golay filter may be used with a cubic polyfit. The window of the filter may be selected empirically in some examples. The length of the window may be based, at least in part, on the ultrasound data to be analyzed. For example, a 9-point window may be used for strain measurements in some applications and a 5-point window may be used for volume measurements in some applications. In some examples, the length of the window may be selected by a user via the user interface 124. Unlike some other smoothing filters, the Savitsky-Golay filter may reduce noise from the signal at little or no expense to the underlying relevant signal. In some examples, the ultrasound data may be filtered after interpolation to the pre-set number of frames.

In some embodiments, the pressure processor 170 may be implemented by one or more processors and/or application specific integrated circuits. In some embodiments, the pressure processor 170 may include any one or more machine learning models, artificial intelligence algorithms, and/or neural networks. In some examples, pressure processor 170 may include a partial least squares (PLS) model, deep neural network (DNN), a convolutional neural network (CNN), a recurrent neural network (RNN), an autoencoder neural network, or the like, to estimate volume and/or determine the pressure. The model and/or neural network may be implemented in hardware (e.g., neurons are represented by physical components) and/or software (e.g., neurons and pathways implemented in a software application) components. The model and/or neural network implemented according to the present disclosure may use a variety of topologies and learning algorithms for training the model and/or neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a trained algorithm for estimating volume and/or determining the pressure. In some embodiments, the pressure processor 170 may implement a model and/or neural network in combination with other image processing methods (e.g., segmentation, histogram analysis).

In various embodiments, the model(s) and/or neural network(s) may be trained using any of a variety of currently known or later developed learning techniques to obtain a model and/or neural network (e.g., a trained algorithm, transfer function, or hardware-based system of nodes) that is configured to analyze input data in the form of ultrasound images, measurements, and/or statistics. In some embodiments, the model and/or neural network may be statically trained. That is, the model and/or neural network may be trained with a data set and deployed on the pressure processor 170. In some embodiments, the model and/or neural network may be dynamically trained. In these embodiments, the model and/or neural network may be trained with an initial data set and deployed on the pressure processor 170. However, the model and/or neural network may continue to train and be modified based on ultrasound images acquired by the pressure processor 170 after deployment of the model and/or neural network on the pressure processor 170.

In some examples, the ultrasound data may be provided to a model of the pressure processor 170. The model may determine a value of the pressure based on an analysis of the ultrasound data. The ultrasound data may have been pre-processed as described above prior to being provided to the model. The model may include a correlation algorithm that correlates the ultrasound data to a value of pressure. The correlation algorithm may have been trained to generate a transfer function with one or more regression coefficients. In some examples, the transfer function may be a matrix of one or more dimensions. The transfer function may be applied to the ultrasound data to output the value of the pressure. In some examples, the correlation algorithm includes a PLS model. The PLS technique may allow for correlation between a set of multiple inputs (e.g., volume, strain measurements) and a single output (e.g., LVEDP), even when the inputs are linearly correlated with one another. In some examples, the model may include a neural network, such as a Long Short-Term Memory (LSTM) network, in addition to or instead of the PLS model.

Alternatively or in addition to a value of pressure a classifier may be output by the pressure processor 170. For example, a binary classifier (e.g., normal/high), or a multi-level classifier (e.g., normal, mild, moderate, severe). The level of the classifier may be based, at least in part, on whether a value of the pressure is above, equal to, or below one or more threshold values. For example, in the case of a binary classifier, the pressure processor 170 may output "normal" as a level of the classifier if the pressure is below a threshold value and output "high" if the pressure is equal to or above the threshold value. Threshold values for pressure may be based, at least in part, on characteristics of the subject (e.g., sex, age, weight) in some examples.

Optionally, in some examples, the pressure processor 170 may output additional data such as a confidence level associated with the value of the pressure. In some examples, the confidence level may be used to provide additional classifiers. For example, if there is insufficient data and/or the data is too noisy for the pressure processor 170 to determine a value of the pressure with confidence above a threshold value (e.g., 50%, 60%, 80%, 90%, 95%), the classifier returned may be indeterminate (e.g., unknown, invalid). Furthermore, although strain and volume are provided as examples, other ultrasound data may also be provided to the pressure processor 170 for analysis (e.g., blood flow velocity estimates from the heart over a cardiac cycle) to determine the pressure. Additionally, in some examples, non-ultrasound data may also be provided to the pressure processor 170 for analysis (e.g., electrocardiography signals) to determine the pressure.

Outputs from the pressure processor 170, scan converter 130, the multiplanar reformatter 132, and/or the volume renderer 134 may be coupled to an image processor 136 for further enhancement, buffering and temporary storage before being displayed on an image display 138. In some examples, the value of the pressure and/or a classifier associated with the pressure may be shown on the display 138 as text and/or a color. For example, the classifier may be displayed as a circle or other symbol and the color of the symbol may indicate a level of the classifier (e.g., normal=green, mild=yellow, moderate=orange, high=red, unknown/invalid=gray). In some examples, the value of pressure and/or classifier may be shown on the display 138 simultaneously with one or more images (e.g., B-mode image, strain map). A graphics processor 140 may generate graphic overlays for display with the images. These graphic overlays can contain, e.g., standard identifying information such as patient name, date and time of the image, imaging parameters, and the like. For these purposes the graphics processor may be configured to receive input from the user interface 124, such as a typed patient name or other annotations. The user interface 124 can also be coupled to the multiplanar reformatter 132 for selection and control of a display of multiple multiplanar reformatted (MPR) images.

The system 100 may include local memory 142. Local memory 142 may be implemented as any suitable non-transitory computer readable medium (e.g., flash drive, disk drive). Local memory 142 may store data generated by the system 100 including ultrasound images, strain measurements, volume measurements, executable instructions, imaging parameters, training data sets, and/or any other information necessary for the operation of the system 100.

As mentioned previously system 100 includes user interface 124. User interface 124 may include display 138 and control panel 152. The display 138 may include a display device implemented using a variety of known display technologies, such as LCD, LED, OLED, or plasma display technology. In some embodiments, display 138 may comprise multiple displays. The control panel 152 may be configured to receive user inputs (e.g., pre-set number of frames, filter window length, imaging mode). The control panel 152 may include one or more hard controls (e.g., buttons, knobs, dials, encoders, mouse, trackball or others). In some embodiments, the control panel 152 may additionally or alternatively include soft controls (e.g., GUI control elements or simply, GUI controls) provided on a touch sensitive display. In some embodiments, display 138 may be a touch sensitive display that includes one or more soft controls of the control panel 152.

In some embodiments, various components shown in FIG. 1 may be combined. For instance, image processor 136 and graphics processor 140 may be implemented as a single processor. In some embodiments, various components shown in FIG. 1 may be implemented as separate components. For example, signal processor 126 may be implemented as separate signal processors for each imaging mode (e.g., B-mode, Doppler, SWE). In some embodiments, one or more of the various processors shown in FIG. 1 may be implemented by general purpose processors and/or micro-processors configured to perform the specified tasks. In some embodiments, one or more of the various processors may be implemented as application specific circuits. In some embodiments, one or more of the various processors (e.g., image processor 136) may be implemented with one or more graphical processing units (GPU).

Figure 2:
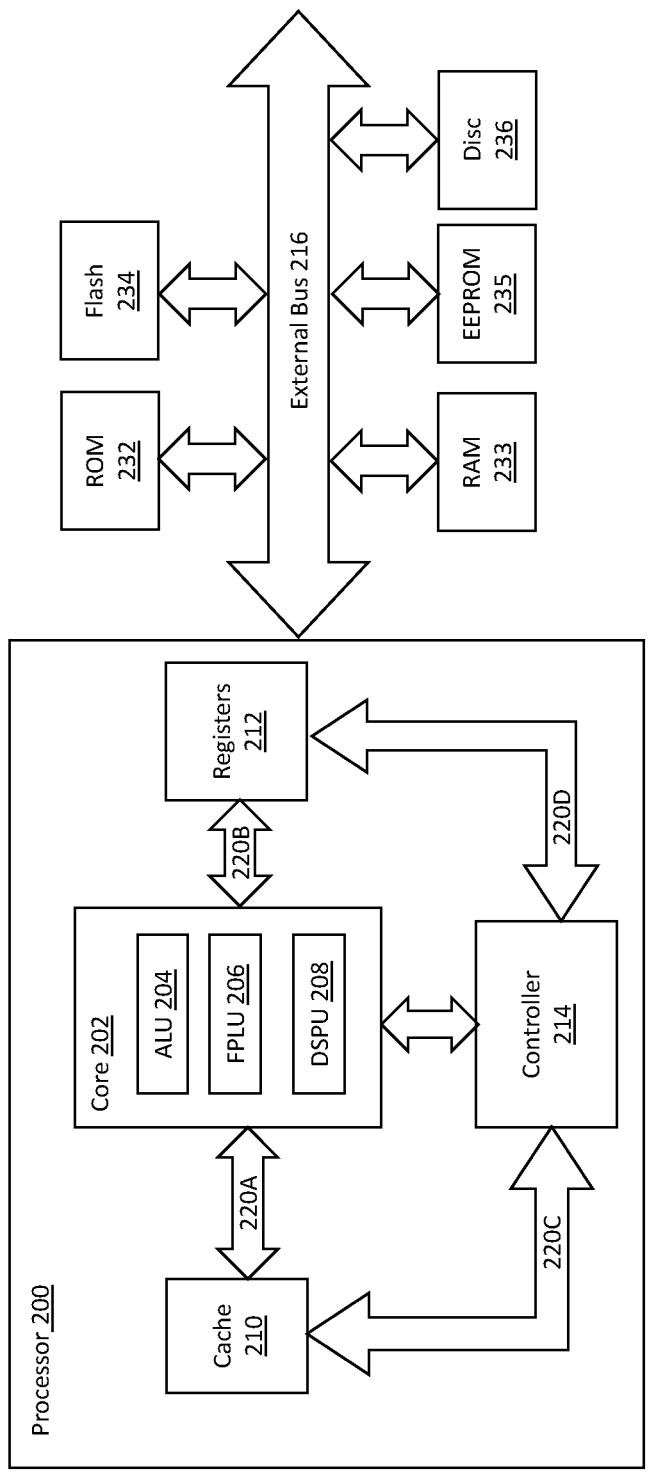
FIG. 2 is a block diagram illustrating an example processor in accordance with principles of the present disclosure.

FIG. 2 is a block diagram illustrating an example processor 200 according to principles of the present disclosure. Processor 200 may be used to implement one or more processors and/or controllers described herein, for example, image processor 136 shown in FIG. 1 and/or any other processor or controller shown in FIG. 1. Processor 200 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 200 may include one or more cores 202. The core 202 may include one or more arithmetic logic units (ALU) 204. In some embodiments, the core 202 may include a floating point logic unit (FPLU) 206 and/or a digital signal processing unit (DSPU) 208 in addition to or instead of the ALU 204.

The processor 200 may include one or more registers 212 communicatively coupled to the core 202. The registers 212 may be implemented using dedicated logic gate circuits (e.g., flip-flops) and/or any memory technology. In some embodiments the registers 212 may be implemented using static memory. The register may provide data, instructions and addresses to the core 202.

In some embodiments, processor 200 may include one or more levels of cache memory 210 communicatively coupled to the core 202. The cache memory 210 may provide computer-readable instructions to the core 202 for execution. The cache memory 210 may provide data for processing by the core 202. In some embodiments, the computer-readable instructions may have been provided to the cache memory 210 by a local memory, for example, local memory attached to the external bus 216. The cache memory 210 may be implemented with any suitable cache memory type, for example, metal-oxide semiconductor (MOS) memory such as static random access memory (SRAM), dynamic random access memory (DRAM), and/or any other suitable memory technology.

The processor 200 may include a controller 214, which may control input to the processor 200 from other processors and/or components included in a system (e.g., control panel 152 and scan converter 130 shown in FIG. 1) and/or outputs from the processor 200 to other processors and/or components included in the system (e.g., display 138 and volume renderer 134 shown in FIG. 1). Controller 214 may control the data paths in the ALU 204, FPLU 206 and/or DSPU 208. Controller 214 may be implemented as one or more state machines, data paths and/or dedicated control logic. The gates of controller 214 may be implemented as standalone gates, FPGA, ASIC or any other suitable technology.

The registers 212 and the cache memory 210 may communicate with controller 214 and core 202 via internal connections 220A, 220B, 220C and 220D. Internal connections may implemented as a bus, multiplexor, crossbar switch, and/or any other suitable connection technology.

Inputs and outputs for the processor 200 may be provided via a bus 216, which may include one or more conductive lines. The bus 216 may be communicatively coupled to one or more components of processor 200, for example the controller 214, cache memory 210, and/or register 212. The bus 216 may be coupled to one or more components of the system, such as display 138 and control panel 152 mentioned previously.

The bus 216 may be coupled to one or more external memories. The external memories may include Read Only Memory (ROM) 232. ROM 232 may be a masked ROM, Electronically Programmable Read Only Memory (EPROM) or any other suitable technology. The external memory may include Random Access Memory (RAM) 233. RAM 233 may be a static RAM, battery backed up static RANI, Dynamic RANI (DRAM) or any other suitable technology. The external memory may include Electrically Erasable Programmable Read Only Memory (EEPROM) 235. The external memory may include Flash memory 234. The external memory may include a magnetic storage device such as disc 236. In some embodiments, the external memories may be included in a system, such as ultrasound imaging system 100 shown in FIG. 1, for example local memory 142.

Figure 3:
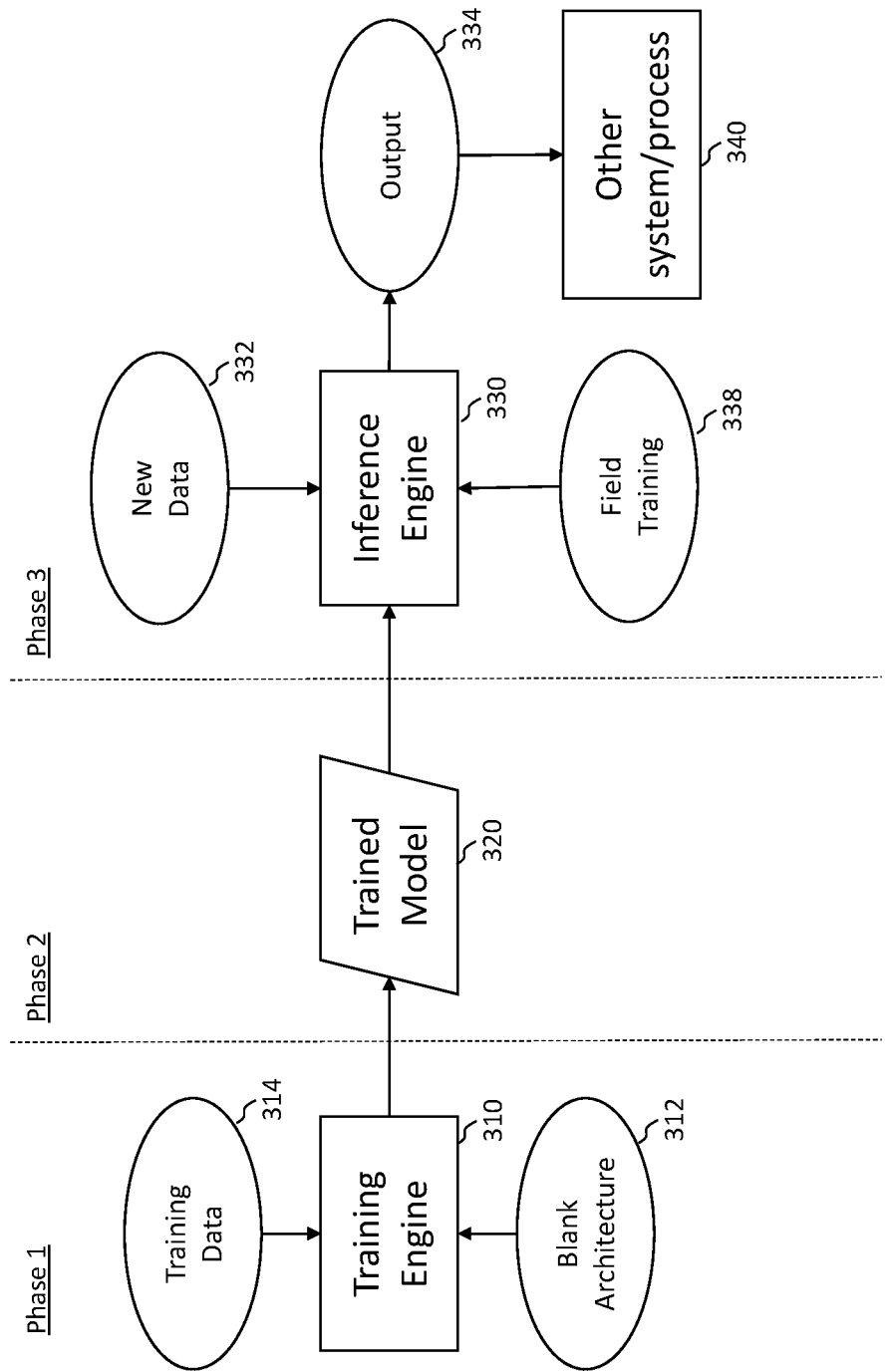
FIG. 3 is a block diagram of a process for training and deployment of a neural network in accordance with the principles of the present disclosure.

FIG. 3 shows a block diagram of a process for training and deployment of a model such as a correlation algorithm and/or a neural network (e.g., PLS, LSTM) in accordance with the principles of the present disclosure. The process shown in FIG. 3 may be used to train a model included in the pressure processor 170. The left hand side of FIG. 3, phase 1, illustrates the training of a model. To train the model, training sets which include multiple instances of input arrays and output classifications may be presented to the training algorithm(s) of the model(s) (e.g., AlexNet training algorithm, as described by Krizhevsky, A., Sutskever, I. and Hinton, G. E. "*ImageNet Classification with Deep Convolutional Neural Networks*," NIPS 2012 or its descendants). Training may involve the selection of a starting algorithm and/or network architecture 312 and the preparation of training data 314. The starting architecture 312 may be a blank architecture (e.g., an architecture with defined layers and arrangement of nodes but without any previously trained weights, a defined algorithm with or without a set number of regression coefficients) or a partially trained model, such as the inception networks, which may then be further tailored for analysis of ultrasound data. The starting architecture 312 (e.g., blank weights) and training data 314 are provided to a training engine 310 for training the model. Upon sufficient number of iterations (e.g., when the model performs consistently within an acceptable error), the model 320 is said to be trained and ready for deployment, which is illustrated in the middle of FIG. 3, phase 2. The right hand side of FIG. 3, or phase 3, the trained model 320 is applied (via inference engine 330) for analysis of new data 332, which is data that has not been presented to the model during the initial training (in phase 1). For example, the new data 332 may include unknown data such as live ultrasound images acquired during a scan of a patient (e.g., cardiac images during an echocardiography exam). The trained model 320 implemented via engine 330 is used to analyze the unknown data in accordance with the training of the model 320 to provide an output 334 (e.g., a border of the LA, a value of pressure.). The output 334 may then be used by the system for subsequent processes 340 (e.g., determining a volume of the LA from the border, outputting text of the pressure on a display).

In the embodiments where the trained model 320 is used to implement a model of the pressure processor 170, the starting architecture may be that of a convolutional neural network, or a deep convolutional neural network in some examples, which may be trained to generate the border of the LA, LV, and/or other heart chamber. The training data 314 may include multiple (hundreds, often thousands or even more) annotated/labeled images, also referred to as training images. It will be understood that the training image need not include a full image produced by an imaging system (e.g., representative of the full field of view of an ultrasound probe) but may include patches or portions of images, for example, those portions that include the LA.

In embodiments where the trained model 320 is used to implement a model of the pressure processor 170, the starting architecture may be that of a PLS model and/or a LSTM network in some examples, which may be trained to generate a value and/or a classifier for the pressure. The training data 314 may include multiple ultrasound data sets (e.g., strain curves, volumes, etc.) annotated/labeled with the pressure measured by a catheter or other means. In some examples, the training data 314 may be preprocessed as described with reference to FIG. 1 prior to being provided to the training engine 310. In some examples, the ultrasound data sets may be annotated/labeled with a classifier (e.g., high, low). In some examples, the ultrasound data sets may be annotated/labeled with both the classifier and the value of the pressure.

In some examples, training may include providing a training data set, a validation data set, and a test data set. The training data set may be used for algorithm building (e.g., finding the weights of the coefficients in the PLS and/or LSTM network). The validation data set may be used to optimize the model after training to avoid overfitting to the training data set. For example, when a loss function of the validation data set increases for three consecutive training epochs, training may be stopped. Finally, the trained model may be tested on the test data set. In some applications, additional data may be used for training the LSTM network compared to the PLS model.

In various embodiments, the trained model(s) may be implemented, at least in part, in a computer-readable medium comprising executable instructions executed by a processor, e.g., pressure processor 170.

Figure 5:
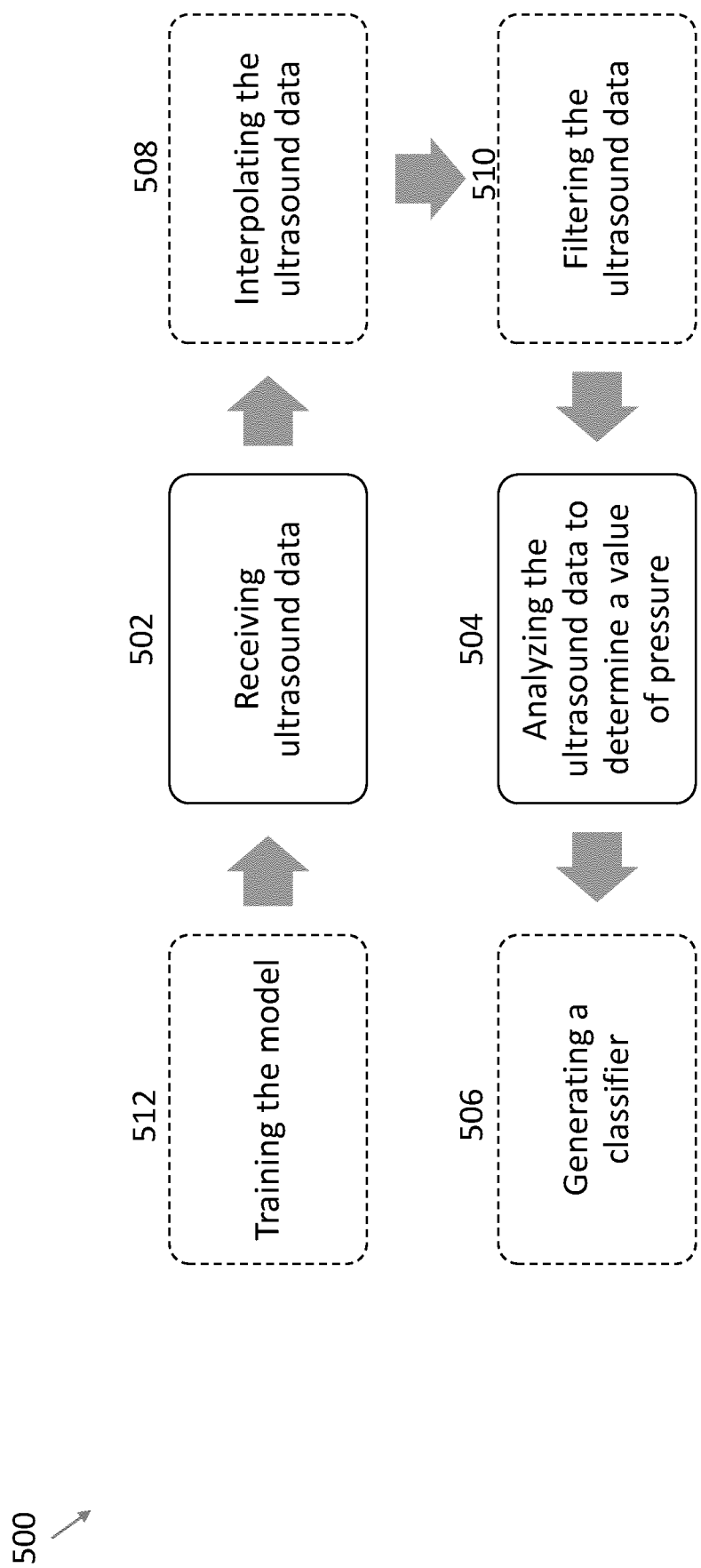
FIG. 5 is a flow chart of a method in accordance with the principles of the present disclosure.

FIG. 5 is a flow chart of a method 500 in accordance with the principles of the present disclosure. In some examples, the method 500 may be performed by the ultrasound imaging system 100 and/or portions of the ultrasound imaging system (e.g., probe 112, strain processor 166, and/or pressure processor 170).

At block 502, "receiving ultrasound data" may be performed. The ultrasound data may be of a left atrium (LA) of a heart in some examples. However, in other examples, the ultrasound data may be from the left ventricle (LV), another portion of the heart, and/or a combination thereof (e.g., both LA and LV). The ultrasound data may have been acquired across a cardiac cycle, a portion of a cardiac cycle, and/or multiple cardiac cycles in some examples. The ultrasound data may have been acquired from B-mode images, Doppler images, strain measurements, and/or a combination thereof in some examples. The ultrasound data may include strain measurements (e.g., strain curves) and/or volumes (e.g., volume of the LA and/or LV). In some examples, the images and/or strain measurements may have been generated by various processors such as B-mode processor 128, Doppler processor 160, and/or strain processor 166 based, at least in part, on ultrasound signals acquired from ultrasound probe 112.

At block 504, "analyzing the ultrasound data to determine a value of pressure" may be performed. In some examples, the ultrasound data may be analyzed with a correlation algorithm, which may include one or more models. In some examples, the model may include a partial least squares model. In some examples, the model may include a long short-term memory network. In some examples, analyzing the ultrasound data may include applying a transfer function including at least one regression coefficient to the ultrasound data. In some examples, the analyzing may be performed by pressure processor 170. In some examples, the pressure may be a ventricular pressure. In some examples, the pressure may include at least one of LVEDP, filling pressure, or PCWP.

Optionally, at block 506, "generating a classifier" may be performed. In some examples, the classifier may be associated with the value of the pressure. In some examples, the classifier may be a binary classifier. In some examples, the binary classifier has a first level when the value of the pressure is below a threshold value and a second level when the value of the pressure is equal to or above the threshold value. In other examples, the classifier may have more than two levels based, at least in part, on different ranges of values for the pressure. In some examples, the generating may be performed by the pressure processor 170.

In some examples, at block 508, "interpolating the ultrasound data" may be performed. In some examples, the ultrasound data may be interpolated to a pre-set number of frames across a desired acquisition period (e.g., an entire cardiac cycle, across an entire phase or multiple phases of the cardiac cycle) prior to the analyzing in block 504.

In some examples, at block 510, "filtering the ultrasound data" may be performed. The filtering may be performed with a digital filter prior to the analyzing. In some examples, such as the one shown in FIG. 5, the filtering may be performed after the interpolating at block 508. In some examples, the digital filter may include a Savitsky-Golay filter with a cubic polyfit. In some examples, the interpolating and/or filtering may be performed by the pressure processor 170. In some examples, such as when the model includes an LSTM network, some or all of the filtering of the ultrasound data may be omitted. For example, in some applications, the LSTM network may find optimal weights across time-series to find features that are highly important to the input-output relationship, as well ignore other features. Thus, if a large enough data set that is representative to build a robust model is available, some or all filtering of noise may be omitted.

In some examples, prior to block 502, at block 512 "training the model" may be performed. In some examples, the training may be performed with a training data set. The training data set may include an ultrasound dataset labeled with a value of pressure acquired from a catheter. For example, the ultrasound data set may include strain measurements and/or volume measurements associated with a pressure value acquired from the catheter. In some examples, the model may be trained on the ultrasound imaging system 100. In some examples, the model may be trained prior to being deployed (e.g., implemented by the pressure processor 170) on the ultrasound imaging system 100.

The systems and methods disclosed herein may provide a non-invasive technique for determining a value of pressure and/or providing a qualitative assessment of pressure based, at least in part, on ultrasound data. In some applications, this may reduce invasive procedures, time, and/or money for determining the pressure, which may assist in diagnosing late stage cardiac failure and/or other cardiac disorders.

In some applications, use of PLS and/or LSTM network may allow analysis of multiple components from ultrasound data that are correlated and/or dependent on one another, which may provide more reliable results than linear regression techniques. In some applications, use of an LSTM network may reduce sensitivity to varying gaps in time between frames. For example, heart rates (e.g., beats per minute) may vary across an acquisition or across multiple acquisitions used to generate the ultrasound data for analysis. In other examples, acquisition rates (e.g., frame rate) may vary from subject to subject or from scan to scan. Thus, the time points of the frames may be different. In contrast, techniques that use linear regression, the time axis must be known and/or fixed.

Although the examples described herein discuss processing of ultrasound image data, it is understood that the principles of the present disclosure are not limited to ultrasound and may be applied to image data from other modalities such as magnetic resonance imaging and computed tomography.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "C#", "Java", "Python", and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
a processor configured to:
receive ultrasound data from a heart, wherein the ultrasound data was acquired across at least a portion of a cardiac cycle; and
analyze the ultrasound data by applying a correlation algorithm to determine a value of cardiac pressure, wherein the correlation algorithm comprises at least one of a partial least squares model or a long short-term memory network.

2. The ultrasound imaging system of claim 1, wherein the processor is further configured to interpolate the ultrasound data to a pre-set number of frames across the at least the portion of the cardiac cycle.

3. The ultrasound imaging system of claim 1, wherein the processor is further configured to filter the ultrasound data with a digital filter.

4. The ultrasound imaging system of claim 3, wherein the digital filter includes a Savitsky-Golay filter with a cubic polyfit.

5. The ultrasound imaging system of claim 1, wherein the processor is further configured to:
analyze a sequence of two-dimensional ultrasound images with a machine learning model to determine a border of a chamber of the heart in individual ones of the two-dimensional ultrasound images; and
calculate volumes of the chamber, based, at least in part, on the borders of the individual ones of the two-dimensional ultrasound images, wherein the volumes of the chamber are included in the ultrasound data.

6. The ultrasound imaging system of claim 1, wherein the processor is further configured to:
analyze a sequence of three-dimensional ultrasound images with a machine learning model to determine a border of a chamber of the heart in individual ones of the three-dimensional ultrasound images; and calculate volumes of the chamber, based, at least in part, on the borders of the individual ones of the three-dimensional ultrasound images, wherein the volumes of the chamber are included in the ultrasound data.

7. The ultrasound imaging system of claim 1, further comprising:

a strain processor configured to generate strain measurements based, at least in part on ultrasound signals received from the heart, wherein the strain measurements are included in the ultrasound data.

8. The ultrasound imaging system of claim 1, wherein the processor is further configured to generate a classifier associated with the value of the cardiac pressure.

9. A method comprising:

receiving ultrasound data from a heart, wherein the ultrasound data was acquired across a cardiac cycle; and analyzing the ultrasound data by applying a correlation algorithm to determine a value of cardiac pressure, wherein the correlation algorithm includes a model, wherein the model includes at least one of a partial least squares model or a long short-term memory network.

10. The method of claim 9, further comprising interpolating the ultrasound data to a pre-set number of frames across the cardiac cycle prior to the analyzing.

11. The method of claim 9, further comprising filtering the ultrasound data with a digital filter prior to the analyzing, wherein the digital filter comprises a Savitsky-Golay filter with a cubic polyfit.

12. The method of claim 9, wherein the ultrasound data includes at least one of strain measurements or volumes.

13. The method of claim 9, further comprising generating a classifier associated with at least one of the value of the cardiac pressure or a confidence level in the value of the cardiac pressure.

14. The method of claim 13, wherein the classifier is a binary classifier and the binary classifier has a first level when the value of the pressure is below a threshold value and a second level when the value of the cardiac pressure is equal to or above the threshold value.

15. The method of claim 9, further comprising training the model with a training data set, wherein the training data set comprises an ultrasound dataset labeled with a value of the cardiac pressure acquired from a catheter.

16. The method of claim 9, wherein the analyzing comprises applying a transfer function including at least one regression coefficient to the ultrasound data.

17. The method of claim 9, where the ultrasound data is from at least one of a left atrium or a left ventricle of the heart.

18. A non-transitory computer-readable medium containing instructions, that when executed, causes an imaging system to:

receive ultrasound data from a heart, wherein the ultrasound data was acquired across at least a portion of a cardiac cycle;

interpolate the ultrasound data to a pre-set number of frames over the cardiac cycle;

filter the ultrasound data with a digital filter after interpolating; and analyze the ultrasound data by applying a correlation algorithm to determine a value of cardiac pressure after filtering, wherein the correlation algorithm comprises at least one of a partial least squares model or a long short-term memory network.

* * * * *